(12) United States Patent
Okita

(10) Patent No.: US 10,898,066 B2
(45) Date of Patent: Jan. 26, 2021

(54) LIGHT ADJUSTMENT APPARATUS AND OPTICAL EQUIPMENT MOUNTING LIGHT ADJUSTMENT APPARATUS THEREON

(71) Applicant: OLYMPUS CORPORATION, Tokyo (JP)

(72) Inventor: Tatsuhiko Okita, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 368 days.

(21) Appl. No.: 15/958,166

(22) Filed: Apr. 20, 2018

(65) Prior Publication Data
US 2018/0235452 A1 Aug. 23, 2018

Related U.S. Application Data

(63) Continuation of application No. PCT/JP2015/080426, filed on Oct. 28, 2015.

(51) Int. Cl.
*A61B 1/06* (2006.01)
*G03B 9/02* (2006.01)
(Continued)

(52) U.S. Cl.
CPC ........... *A61B 1/0661* (2013.01); *A61B 1/045* (2013.01); *A61B 1/06* (2013.01); *G02B 23/2476* (2013.01);
(Continued)

(58) Field of Classification Search
CPC ......... A61B 1/0061; A61B 1/045; A61B 1/06; G02B 23/2476; G02B 23/26; G02B 26/023; G03B 9/02
See application file for complete search history.

(56) References Cited

U.S. PATENT DOCUMENTS 6,829,076 B2 * 12/2004 Fukushima ............ H02K 26/00
                                                                                        359/237
8,134,768 B2 *  3/2012 Ide .......................... G03B 5/02
                                                                                        359/234
(Continued)

FOREIGN PATENT DOCUMENTS

JP          H10-20360 A      1/1998
JP       2007-295771 A      11/2007
(Continued)

OTHER PUBLICATIONS

International Search Report dated Jan. 26, 2016 issued in PCT/JP2015/080426.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

The light adjustment apparatus of the present embodiment comprises a light adjustment part, a rotation axis body that supports a rotation arm that places and removes the light adjustment part in and out of a light path by swinging, and has a magnet installed therein, an electromagnetic drive source that forms a magnetic circuit including the rotation axis body on the circuit, and works an electromagnetic force on the magnet to rotate a rotational axis of the rotation axis body, and a float prevention part that magnetically restricts the rotation axis body, and prevents the rotation axis body from floating towards an axial direction of the rotational axis when the rotation axis body is rotated.

3 Claims, 7 Drawing Sheets

(51) Int. Cl.
*A61B 1/045* (2006.01)
*G02B 23/24* (2006.01)
*G02B 26/02* (2006.01)
*G02B 23/26* (2006.01)

(52) U.S. Cl.
CPC ........... *G02B 23/26* (2013.01); *G02B 26/023* (2013.01); *G03B 9/02* (2013.01); *G03B 2205/0069* (2013.01)

(56) References Cited

U.S. PATENT DOCUMENTS

| | | | | |
|---|---|---|---|---|
| 9,684,224 | B2* | 6/2017 | Okita | G03B 9/02 |
| 2004/0036798 | A1* | 2/2004 | Saito | H04N 5/2251 |
| | | | | 348/363 |
| 2004/0222709 | A1* | 11/2004 | Naganuma | G03B 7/10 |
| | | | | 310/36 |
| 2008/0055027 | A1* | 3/2008 | Kayama | G03B 9/10 |
| | | | | 335/222 |
| 2008/0278963 | A1* | 11/2008 | Mizuno | H04N 5/2354 |
| | | | | 362/552 |
| 2012/0002309 | A1* | 1/2012 | Okita | G02B 5/005 |
| | | | | 359/824 |
| 2017/0023845 | A1* | 1/2017 | Matsuki | G02B 5/005 |
| 2018/0246319 | A1* | 8/2018 | Kitanaka | G02B 7/005 |

FOREIGN PATENT DOCUMENTS

JP 2007295771 A * 11/2007
JP 2010-113092 A 5/2010

OTHER PUBLICATIONS

English translation of International Preliminary Report on Patentability dated May 11, 2018 together with the Written Opinion received in related International Application No. PCT/JP2015/080426.

* cited by examiner

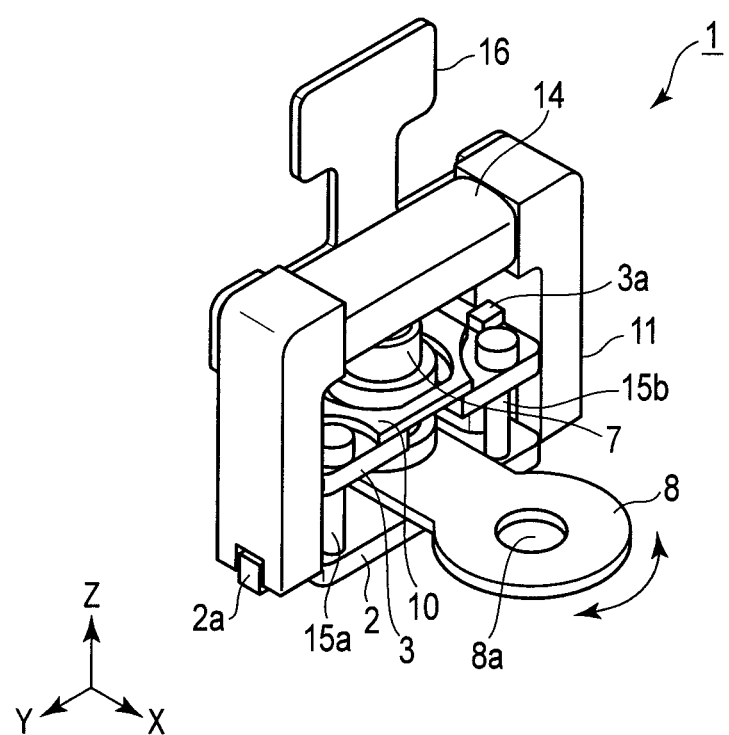
F I G. 1

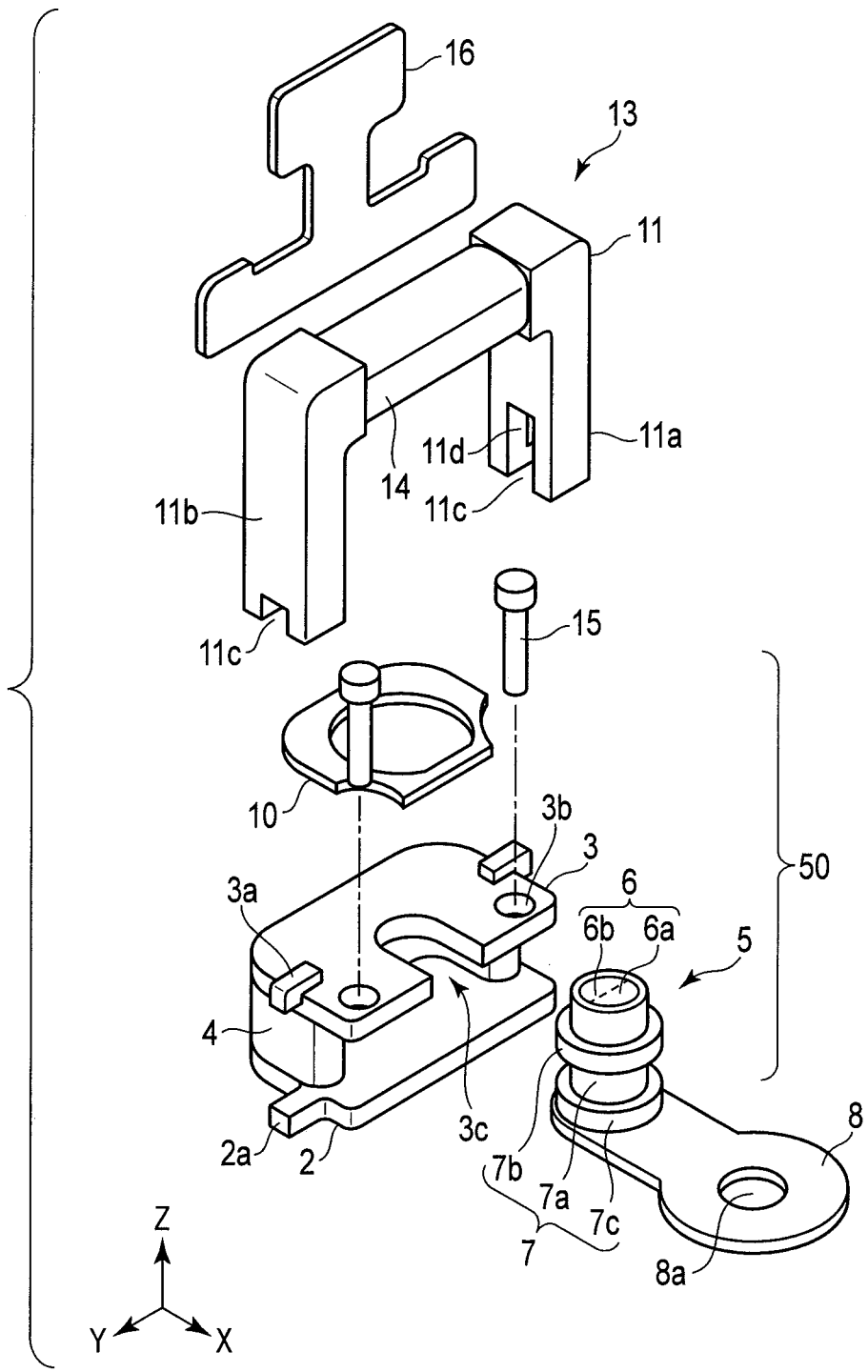
F I G. 2A

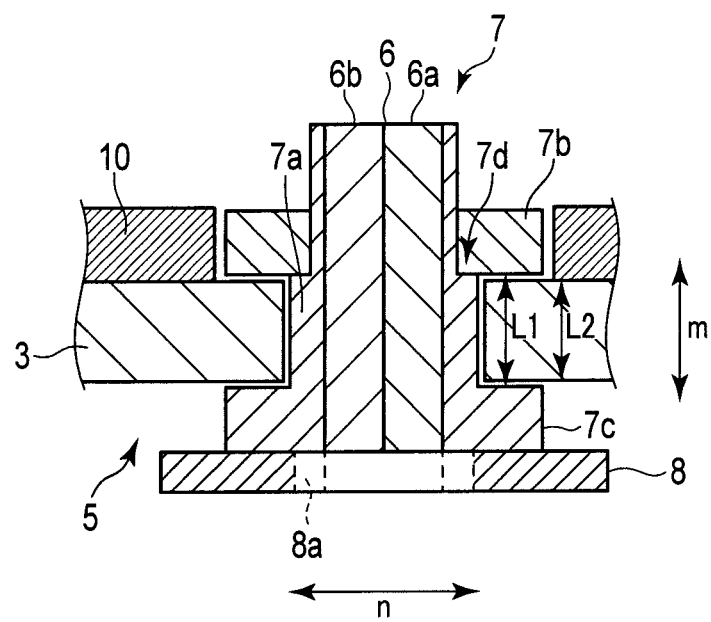
F I G. 4
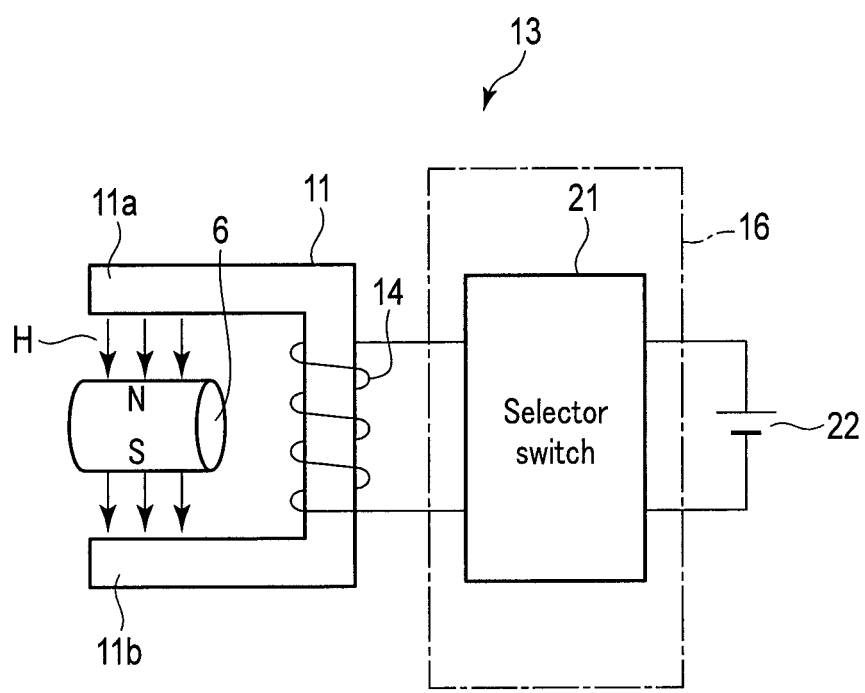
F I G. 5

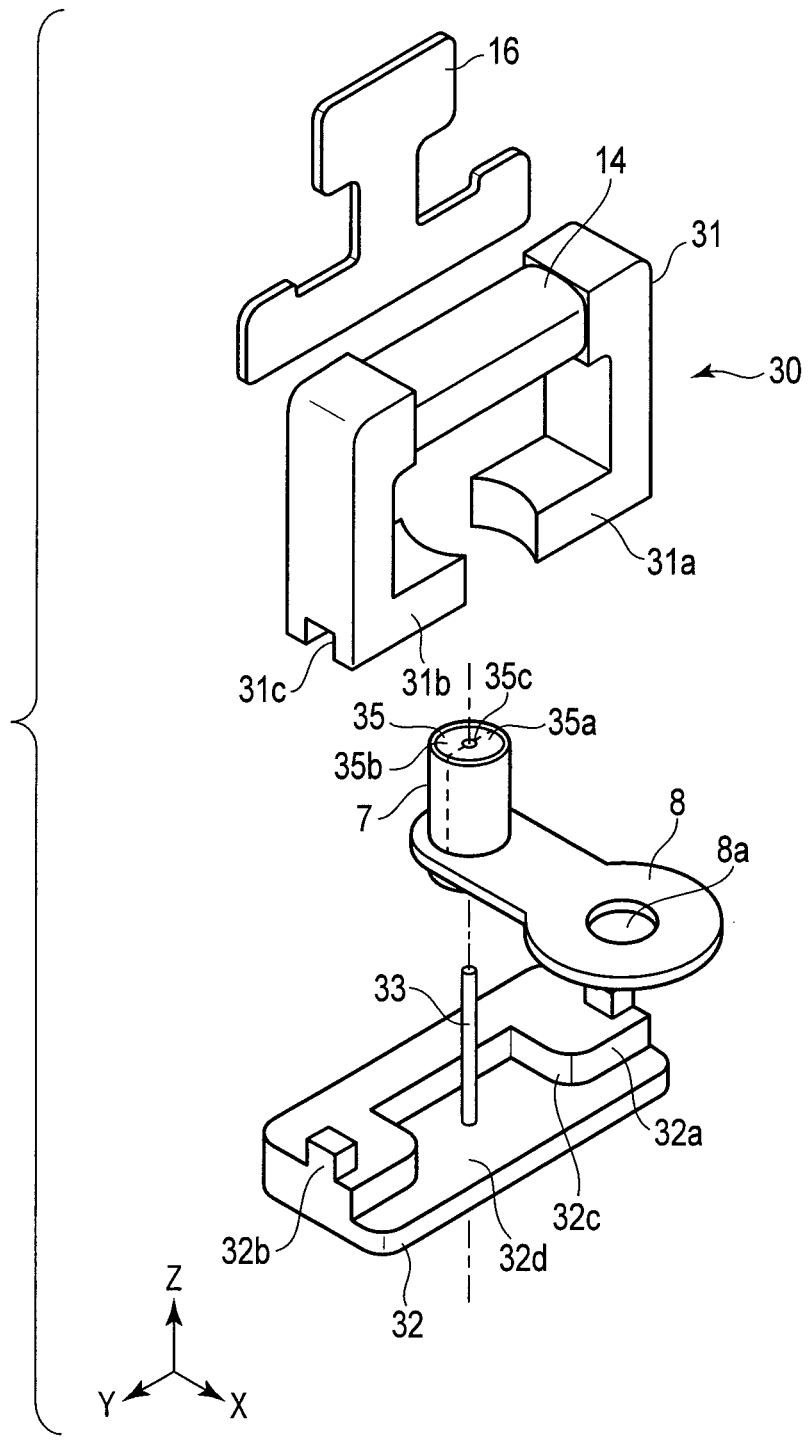
F I G. 7

LIGHT ADJUSTMENT APPARATUS AND OPTICAL EQUIPMENT MOUNTING LIGHT ADJUSTMENT APPARATUS THEREON

CROSS-REFERENCE TO RELATED APPLICATIONS

This is a Continuation Application of PCT Application No. PCT/JP2015/080426, filed Oct. 28, 2015, which was published under PCT Article 21(2) in Japanese.

BACKGROUND OF THE INVENTION

1. Field of the Invention

The present invention relates generally to a light adjustment apparatus that inserts/removes a light adjustment element into/from a light path, and optical equipment mounting the light adjustment apparatus thereon, in which the light adjustment element acts on a light flux or a light image transmissive through the light path.

2. Description of the Related Art

Generally, a light adjustment element known as a diaphragm or a filter, etc. is arranged on a light path of optical equipment, and acts on a passing light flux in a manner suitable for each purpose. In addition to a configuration in which the light adjustment element is fixed on the light path, in a case where a configuration that retracts the light adjustment element from the light path is required, a light adjustment apparatus being a combination of the light adjustment element and a movement mechanism is mounted on the optical equipment.

As an example of a light adjustment apparatus used for a camera, etc. serving as optical equipment, Jpn. Pat. Appln. KOKAI Publication No. 10-20360 discloses a light amount adjustment apparatus utilizing a print substrate technique. In this light amount adjustment apparatus, a hole at the center of a ring-shaped substrate is utilized as a light path, and a coil body in a wiring pattern is provided around the 0 hole on the substrate. Inside the hole formed adjacent to this coil body, a blade member, which is a light adjustment element that is supported by one hand of a rotor formed of a cylindrical magnet, is provided. This substrate is stored in an upper cover and a lower cover. Here, the blade member is penetrated through a shaft integrally with the rotor, and is fitted to a shaft bearing provided on each of the upper cover and the lower cover to be held rotatably. In such configuration, the blade member is swung between a position blocking the light path and a position retracted to the side by a magnetic force generated by the coil body. Furthermore, a damping groove and a rib are provided inside the upper cover so as to come in contact with the rib to become a guide of a swing operation of the blade member.

BRIEF SUMMARY OF THE INVENTION

According to an embodiment of the present invention, there is provided a light adjustment apparatus that acts on a light flux passing through a light path on the light path, the light adjustment apparatus comprising: a blade member that has a distal end and a proximal end, and is placed into and removed from the light path by being rotated about the proximal end in a direction perpendicular to the light path; a light adjustment member that is provided on the blade member, and acts on the light flux when it is positioned on the light path by rotating the blade member; a rotation axis body that comprises a magnet, is provided on the proximal end of the blade member, and is formed in a manner that a hole is produced at a position of a central axis; a shaft that is inserted in the hole and holds the rotation axis body rotatably; a support substrate that supports the shaft; and a yoke that holds the rotation axis body in a floated state with respect to the support substrate by receiving a magnetic force of the magnet included in the rotation axis body, and is provided facing a side surface of the rotation axis body.

According to the present invention, a light adjustment apparatus that would realize, by a compact size and a simple driving mechanism, a stable swing operation in which the light adjustment element is free from floating or rattling, and optical equipment which has the light adjustment apparatus mounted thereon can be provided.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view showing an outer structure of a light adjustment apparatus according to a first embodiment observed from diagonally above.

FIG. 2A is an exploded configuration diagram of the light adjustment apparatus.

FIG. 4 is a diagram showing a cross section configuration of a swing assembly of the light adjustment apparatus.

FIG. 5 is a diagram showing a configuration of a drive power source part in the light adjustment apparatus.

FIG. 7 is an exploded configuration diagram of a light adjustment apparatus according to a second embodiment.

DETAILED DESCRIPTION OF THE INVENTION

Hereinafter, embodiments of the present invention will be explained in detail with reference to the drawings.

First Embodiment

Figure 2B:
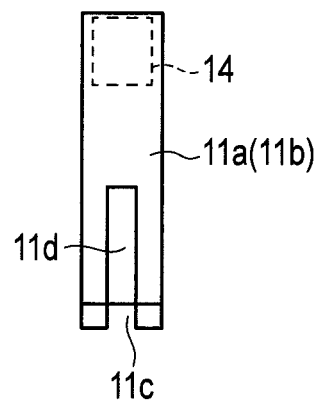
FIG. 2B shows a configuration of a yoke.
Figure 3:
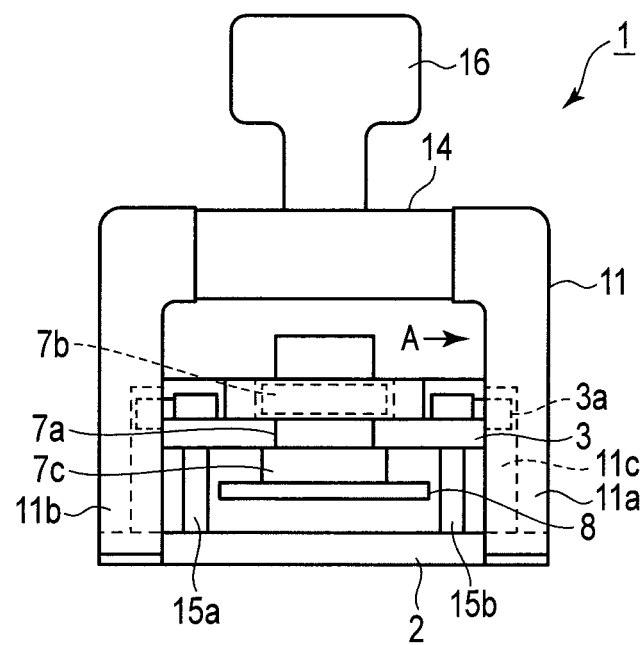
FIG. 3 is a diagram showing an outer structure of the light adjustment apparatus observed from the front.

A light adjustment apparatus according to a first embodiment will be explained. FIG. 1 is a perspective view showing an outer structure of the light adjustment apparatus according to the first embodiment observed from diagonally above; FIG. 2A is an exploded configuration diagram showing the light adjustment apparatus; and FIG. 2B is a diagram showing a cross section configuration of a yoke. Furthermore, FIG. 3 is a diagram showing an outer structure of the light adjustment apparatus observed from the front; FIG. 4 is a diagram showing a cross section configuration of a swing assembly of the light adjustment apparatus in FIG. 1, whose cross-sectional surface cut in an axis Y direction is observed from a front side; and FIG. 5 is a diagram showing a configuration of a drive power source part in the light adjustment apparatus.

In the explanation of each following embodiment, as shown in FIG. 1, an optical axis direction of a light path would be described as an axis Z direction, and directions orthogonal to the axis Z direction would be described as an axis X direction (front side) and an axis Y direction (side surface side). As optical equipment on which a light adjustment apparatus 1 of the present embodiment is mounted, at least an imaging apparatus (imaging optical system), an illumination apparatus, a microscope, an optical measurement apparatus, and an optical readout apparatus (bar code reader, etc.), etc. can be named. Furthermore, optical equipment on which optical equipment comprised of the imaging apparatus will be explained.

This light adjustment apparatus 1 comprises a drive mechanism 50 including a rotation arm part 8, and an electromagnetic drive source 13 that is vertically installed in a joined manner with both side surfaces of this drive mechanism 50, and that forms a magnetic circuit that is explained later on.

As shown in FIG. 2A, the drive mechanism 50 comprises a support member which is configured integrally by interposing a U-shaped spacer 4 at the back of a lower side substrate 2 of a plate, over which an upper side substrate 3 is placed in parallel with the lower side substrate 2. A swing assembly 5 that rotates about the axis Z is assembled on the lower side substrate 2 and the upper side substrate 3. The swing assembly 5 is comprised of a columnar magnet (rotation axis member) 6, a rotation axis body 7 with magnetic permeability that fits the magnet 6 therein, and the rotation arm part (blade member) 8 that is attached to the bottom of the rotation axis body 7.

The lower side substrate 2 and the upper side substrate 3 are formed into a same rectangular plate shape using a hard material. In the present embodiment, the outer shapes of the lower side substrate 2 and the upper side substrate 3 are the same. However, this is a matter of design. Therefore, the shape and size of each substrate would be changed as appropriate depending on an installation space of equipment on which the apparatus is to be mounted.

On the upper side substrate 3, a U-shaped notch part 3c is formed on the front side, and, on each of both sides thereof, two holes 3b are formed to fit stoppers 15 (15a, 15b) therein in order to restrict a swing range (swing angle) of the rotation arm part 8 explained later on. On both side surfaces of the upper side substrate 3, protruded parts 3a are provided to fit therein fixation grooves 11d of a yoke 11, which is a magnetic flux passage part explained later on, and to perform positioning of an angle direction in which the yoke 11 is to be vertically installed. Furthermore, instead of this joint structure, a notch may be formed on both side surfaces of the upper side substrate 3 to fit protruding parts therein that are formed on the yoke 11 side. A vertical installation angle of the yoke 11 in the present embodiment is set to an angle that becomes parallel to a rotational axis direction of the rotation axis body 7 (or an angle that becomes perpendicular to a surface direction of the upper side substrate 3). However, of course, this angle is not limited, and may be changed as appropriate within a range that allows to form a mounting space of the optical equipment on which the light adjustment apparatus is to be mounted, and a magnetic circuit for driving the rotation axis body 7 explained later.

On both side surfaces of the lower side substrate 2, protruded parts 2a are provided in an extended manner to fit therein fixation grooves 11c of the yoke 11 explained later on, and to perform positioning in a plane surface direction (X-Y surface) and the positioning of the height thereof with respect to the drive mechanism 50.

Furthermore, as shown in FIG. 3, the height of the spacer 4 at the back of the lower side substrate 2 defines a distance between the lower side substrate 2 and the upper side substrate 3, and is set so that the rotation arm part 8 at least does not come in contact with the lower side substrate 2.

The rotation axis body 7 is comprised of an axis body 7a, an upper flange part 7b, and a lower flange part 7c, all of which are hollow and cylindrical, and are formed of a metallic material. The upper flange part 7b and the lower flange part 7c are provided around the axis body 7a with an interval distance L1 (FIG. 4) that will be explained later on. The axis body 7a of the rotation axis body 7 is fitted rotatably into the notch part 3c of the upper side substrate 3. Subsequently, a frame 10 is fixed on an upper surface of the upper side substrate 3. The frame 10 is provided to prevent the rotation axis body 7 from being displaced from the notch part 3c. Furthermore, by fitting the axis body 7a into the notch part 3c, a shift to an n direction shown in FIG. 4, in other words, rattling, can be prevented.

The upper flange part 7b and the lower flange part 7c regulate this rotation axis body 7 so as to be installed perpendicular to the upper side substrate 3, and to set the central axis of the rotation in the axis Z direction. Here, the central axis of the rotation axis body 7 (magnet 6) coincides with the central axis of the swing assembly 5. Hereinafter, the side on which the rotation arm part 8 of the drive mechanism 50 is extended will be referred to as the front, and both sides of the front will be referred to as side surfaces.

Inside the axis body 7a of the rotation axis body 7, the magnet 6 is tightly fitted and is fixed by an adhesive, etc. The magnet 6 is formed to have an outer shape that matches the inner shape of the axis body 7a using a hard-magnetic material such as a ferrite, a neodymium, and a samarium-cobalt, and, here, as an example, is formed columnar. This magnet 6 is bi-polarized by a plane surface passing through the central axis of the circular column serving as a magnetic wall. One of the semicircular columns is magnetized as an N-pole (N-pole part 6a), and the other semicircular column is magnetized as an S-pole (S-pole part 6b).

In this example, a bottom part of the axis body 7a is open and cylindrical. A bottom surface of the magnet 6 and a lower end of the axis body 7a are on the same plane, into which bottom side the rotation arm part 8 is fitted and fixed. The axis body 7a may also be formed into a shape of a cup with a closed bottom.

As shown in FIG. 4, in the present embodiment, the axis body 7a is formed integrally with the lower flange part 7c in a manner extending circumferentially on the lower side. Furthermore, the thickness of the axis body 7a is changed, and a step 7d is provided to make the outer diameter of an upper portion thinner. The upper flange part 7b is fitted in from above until it reaches the step 7d, and is fixed. As this fixation method, for example, an adhesive, welding, or soldering, etc. can be used for adhesion. As long as the rotation arm part 8 is formed of a metallic material, even if an adhesive force weakens, the rotation arm part 8 can be prevented from being detached from the rotation axis body 7 by being adsorbed to a strong magnetic force of the magnet 6. In this example, the axis body 7a and the lower flange part 7c were formed separately and adhered integrally. However, the axis body 7a, the upper flange part 7b, and the lower flange part 7c may also be formed as one part by being shaved away.

The interval distance L1 between the upper flange part 7b and the lower flange part 7c is set to a distance obtained by adding a space that enables rotation with respect to a thickness L2 of the notch part 3c of the upper side substrate 3. The upper flange part 7b and lower flange part 7c also function as a float prevention part with respect to a vertical direction m of the axis Z at the axis body 7a when they are fit into the notch part 3c of the upper side substrate 3, to prevent shifting with respect to the rotational axis direction, that is, to also prevent floating and rattling.

On the other end of the rotation arm part 8 is formed a hole 8a to which an unillustrated light adjustment member (light adjustment element) is fitted and attached. The light adjustment member is, for example, a diaphragm, a shutter, a lens, a shielding plate, or a filter, and may be fixed inside the hole 8a, or may be detachably configured. The rotation arm part 8 of the present embodiment rotates (or swings) in direction n (X axis-Y axis direction) that is orthogonal to an optical axis direction.

Furthermore, as shown in FIG. 2A, pin-shaped stoppers 15 are fitted into the two holes 3b provided on the upper side substrate 3 up to a head part and fixed. As a fixation method, a screw portion may be formed on a distal end part of the stoppers 15 to be screwed into a screw hole (unillustrated) formed on the lower side substrate 2 and attached, or the stoppers 15 may be adhesively fixed by an adhesive, etc. The stoppers 15 define a rotational range (rotational angle) and a stop position of the rotation arm part 8 by abutment of the rotation arm part 8. By the stop position of the hole 8a of the rotation arm part 8, positions of two light paths (optical axis) subject to light adjustment by the light adjustment apparatus 1 is defined. That is, since the present embodiment is not structured to have a position sensor or a configuration for performing rotational position control with respect to the rotation arm part 8, the light path of the light flux (or light image) to be light adjusted would be at a position where it passes through the hole 8a when the rotation arm part 8 is at the stop position. Instead, the mounting position (positions of the holes 3b) of the stoppers 15 of the light adjustment apparatus 1 may of course be set in accordance with the position of the light path in the optical equipment on which the light adjustment apparatus 1 is to be mounted.

In the present embodiment, a stop position at which the rotation arm part 8 shown in FIG. 1 abuts a stopper 15a is a first position, and a stop position at which it abuts a stopper 15b is a second position. Here, a first light path is a light path that passes the hole 8a when the rotation arm part 8 stops at the first position, and a second light path is a light path that passes through the hole 8a when the rotation arm part 8 stops at the second position. There is no need to set a light path at each position. Therefore, one of the positions may be set as a light path position, and the other position may be set as a retreat position. Furthermore, as a light flux to be transmitted in the light path, there are a light image that is formed in a photographic optical system, an illumination light, a visible light, an infrared light, or a ultraviolet light, etc.

As shown in FIG. 5, the electromagnetic drive source 13 is comprised of the yoke 11 that is to be a magnetic flux passage part, a coil 14 that is wound around the yoke 11, a substrate 16 on which a drive circuit including a selector switch 21 connected to both ends of the coil 14 is mounted, and a direct-current power source 22 that supplies direct-current power for driving. The yoke 11 is a magnetically permeable member that is formed into a U-shape by using a conductive material such as steel or a magnetically permeable (soft magnetic) material, on which the coil 14 is tightly wound around a center bottom part of the U-shape. In this example, the coil 14 is arranged at a position facing an upper surface of the upper side substrate 3. However, as long as the coil 14 is provided on the yoke 11 to generate a magnetic flux, the arrangement position would not be limited to a position facing the upper surface of the upper side substrate 3. As shown in FIG. 2A, the yoke 11 is fixed in a manner that the protruded parts 3a of the upper side substrate 3 are fitted to the fixation grooves 11d and passed through, and the protruded parts 2a of the lower side substrate 2 are fitted to the fixation grooves 11c. The substrate 16 may be a hard substrate formed of a hard material, or a flex substrate formed of a resin, etc. In the present embodiment, the substrate 16 is provided adjacent to the coil 14 on a back surface side of the yoke 11.

In the present embodiment, the magnetic flux generated by the coil 14 passes the yoke 11, then a gap of an end part 11a and an end part 11b in which the rotation axis body 7 is arranged. Here, a configuration in which the rotation axis body 7 is incorporated into a magnetic circuit formed by the yoke 11 would be obtained. Details will be explained below.

The selector switch 21 suitably switches a polarity (positive/negative) of a direct-current power supplied from the direct-current power source 22, and applies it to the coil 14. The switching operation of the direct-current power performed by the selector switch 21 is executed in accordance with instructions from a mounted operation part of the equipment.

When a direct-current power is applied, the coil 14 functions as an electromagnet, and provides a magnetic flux H to the yoke 11. The yoke 11 has the magnetic flux H pass therein, forms a magnetic field in a gap between the end parts 11a and 11b, and acts on the magnet 6 within the magnetic field to cause the magnet 6 to generate a suction force or a repulsive force. That is, in the case where the polarity of the magnetic field and the polarity (N-pole, S-pole) of the magnet 6 are the same, a repulsive force is generated to rotate the rotation axis body 7 to an opposite side. In the case where the polarity of the magnetic field and the polarity of the magnet 6 are different, a suction force is generated, and the state is maintained without the rotation axis body 7 being rotated. With the rotation of the rotation axis body 7, the rotation arm part 8 is rotated, and becomes a stopped state by abutting one of the stoppers 15a and 15b. In this configuration, in the case where a bipolar magnet 6 is used, the rotational range (rotational angle) of the rotation arm part 8 is set equal to or larger than 180 degrees. By such rotation of the rotation arm part 8, the first light path and the second light path on which light adjustment is to be performed are switched.

According to the light adjustment apparatus of the present embodiment, the rotation arm part 8 is rotatably provided by a mechanical restraint realized by clamping the upper side substrate 3 vertically by the upper flange part 7b and the lower flange part 7c of the rotation axis body 7 that supports the rotation arm part 8. In this manner, the rotation axis body 7 can be prevented from floating (shifting in an axial direction) when being swung, which would realize the rotation operation of the rotation arm part 8 to be free from contacting other members or wobbling. Similarly, the rotation arm part 8 is rotatably provided by a mechanical restraint in a horizontal direction, which is realized by fitting the axis body 7a of the rotation axis body 7 into the notch part 3c of the upper side substrate 3. Furthermore, since this is a simple configuration with one flange part assembled on the rotation axis body 7 on which a fixed flange part is formed, an assembly error and play in a vertical direction can be suppressed as much as possible upon production, which allows production to be highly accurate.

Furthermore, a portion that comes in contact upon rotation differs depending on the tilt of electronic equipment on which the light adjustment apparatus is mounted. However, since the portion that comes in contact is only one of the contacts of: each facing surface of the upper flange part 7b or the lower lower flange part 7c facing the top and back surfaces of the upper side substrate 3; or an outer peripheral surface of the axis body 7a and an inner surface of the upper side substrate 3, frictional resistance becomes small, which allows a stable rotation operation of the rotation arm part 8 to be realized.

Furthermore, since the support configuration is realized by the clamping between two constituent members, the configuration is hardly affected by the temperature of a surrounding environment. Furthermore, since the yoke 11 and the substrate 16 are installed vertically on the surface of the upper side substrate 3, they are arranged along an optical axis direction in the light adjustment apparatus. This allows an area of a surface that is orthogonal to the optical axis to become small, which would allow the light adjustment apparatus to be easily mounted on electronic equipment that is made small in diameter.

Figure 6:
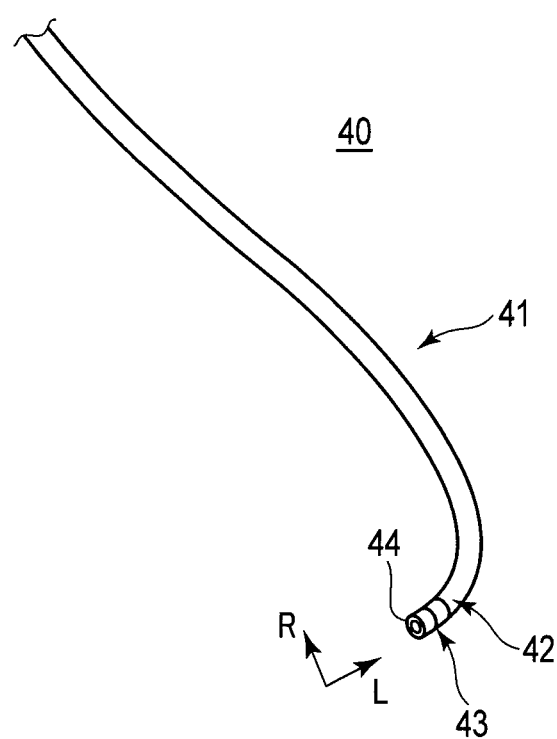
FIG. 6 is a perspective view showing an insertion part of an endoscope on which the light adjustment apparatus is mounted.

As electronic equipment on which the light adjustment apparatus is mounted, FIG. 6 explains an example of mounting the light adjustment apparatus on an insertion part 41 of an endoscope.

The insertion part 41 has a hard part 43 arranged on its distal end, and includes on a proximal end side thereof a curved part 42 that curves in accordance with an operation of an operator, and a flexible part that is continuously provided on the proximal end side of the curved part 42. In FIG. 6, when a longitudinal direction of the curved part 42 is an optical axis direction L (axis Z direction), and a direction which is orthogonal to this optical axis direction L is a radial direction (axis X-axis Y direction) R, the light adjustment apparatus is incorporated inside the hard part 43 so that the upper surface of the upper side substrate 3 shown in FIG. 1 is arranged in the radial direction R, and the electromagnetic drive source 13 is installed vertically in the optical axis direction L.

The hard part 43 is cylindrical and is provided with an imaging window 44 on a distal end surface. On the inside, various units such as an imaging element and an imaging optical system are accommodated. The light adjustment apparatus 1 is incorporated so that at least one of an optical axis of a light image formed in the imaging optical system inside the hard part 43, and a light path (first light path, second light path) defined by the hole 8a of the rotation arm part 8 coincide.

In the hole 8a of the rotation arm part 8 is attached the aforementioned light adjustment part. Here, an example of providing the light adjustment apparatus 1 inside the hard part 43 is given. However, as long as the light image is transmitted through the hole 8a of the rotation arm part 8, the light adjustment apparatus 1 does not have to be limited to being arranged inside the hard part 43, and may be arranged inside an unillustrated operation part provided on the proximal end side of the insertion part.

By incorporating the light adjustment apparatus 1 into the insertion part 41 of the endoscope in the above manner, the insertion part 41 can be made smaller in the radial direction that is orthogonal to the longitudinal direction, which would contribute to making the insertion part 41 thinner. An example of accommodating the light adjustment apparatus 1 inside the hard part 43 in a state where the electromagnetic drive source 13 is installed vertically with respect to the drive mechanism 50 has been explained. However, in the case where the other constituent parts interfere when accommodating the light adjustment apparatus 1, it is also possible to set the electromagnetic drive source 13 appropriately in a tilted manner.

Second Embodiment

Now, a light adjustment apparatus according to a second embodiment will be explained.

Figure 8:
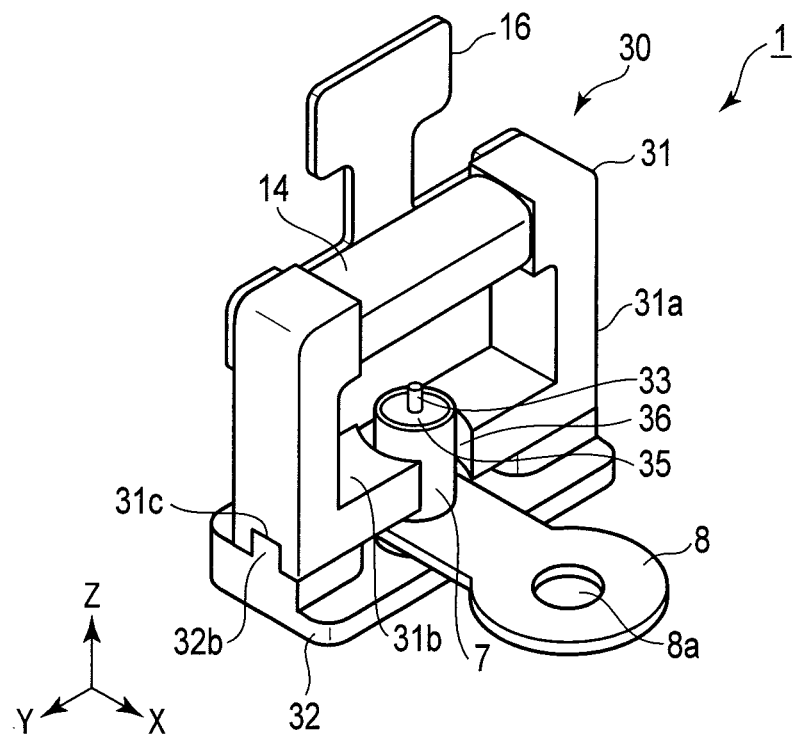
FIG. 8 is a perspective view showing an outer structure of the light adjustment apparatus observed from diagonally above.
Figure 9:
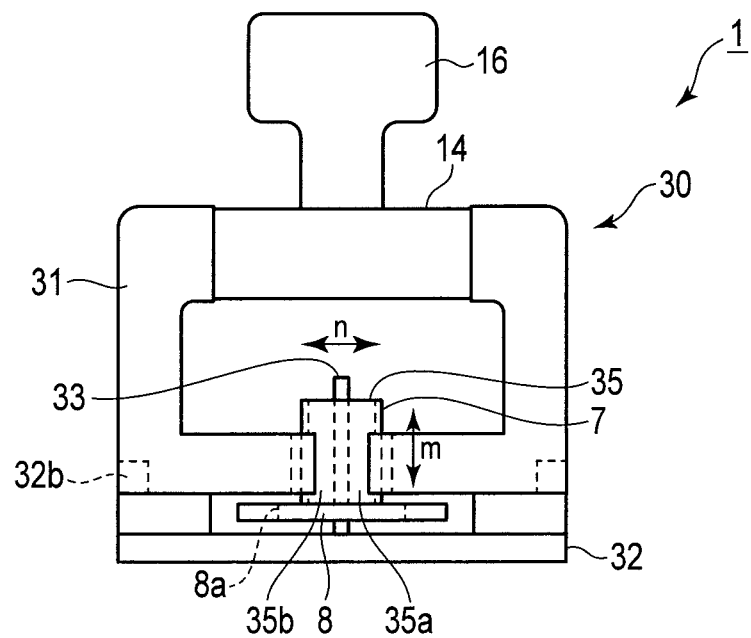
FIG. 9 is a diagram showing an outer structure of the light adjustment apparatus observed from the front.

FIG. 7 is a perspective view showing an exploded configuration of the light adjustment apparatus according to the second embodiment. FIG. 8 is a perspective view showing an outer structure of the light adjustment apparatus. FIG. 9 is a diagram showing an outer structure of the light adjustment apparatus when observed from the front. In the explanation of the present embodiment, the structural parts equivalent to those of the first embodiment are denoted by the same reference symbols, and detailed explanations are omitted.

The light adjustment apparatus of the present embodiment has a different holding structure from the rotation axis body 7 in the drive mechanism of the aforementioned first embodiment. This rotation axis body 7 is fitted onto a shaft installed vertically on a support substrate 32, and is arranged inside a magnetic circuit formed by a yoke formed of a conductive material or a magnetically permeable (soft magnetic) material so as to be held rotatably by a magnetic force. The support substrate 32 has a structure in which the aforementioned lower side substrate 2 and spacer 4 are integrally formed.

The support substrate 32 includes a U-shaped space portion 32a corresponding to the spacer 4, and, is provided with protrusion parts 32b for positioning a fixed position of a yoke 31 respectively on each side surface side of an upper surface of the space portion 32a. At the center of a base surface 32d that is one step lower on the support substrate 32, a thin straight shaft 33 is installed perpendicularly. Furthermore, both inner side corner parts 32c on the front of the space portion 32a are rounded so that the rotation arm part 8 is abutted thereagainst when being rotated. In this manner, the inner side corner parts 32c function as stoppers for stopping the rotation arm part 8 at a light path position. Furthermore, aside from this, the stoppers shown in FIG. 1 may also be installed vertically on both sides.

The rotation axis body 7 is formed hollow and cylindrical by a metallic material. A cylindrical magnet 35 is fitted and mounted therein, and the rotation arm part 8 is fixed on the bottom surface side thereof. In the same manner as the aforementioned magnet 6, this magnet 35 is bi-polarized by a plane surface passing through the central axis of the circular column serving as a magnetic wall. One of the semicircular columns is magnetized as an N-pole (N-pole part 35a), and the other semicircular column is magnetized as an S-pole (S-pole part 35b). Furthermore, a hole 35c for fitting the shaft 33 therein is formed at a position of a central axis on the magnet 35.

The yoke 31 is formed into a frame-like shape with a notch, in which extending parts 31a and 31b are provided inwards from both end parts on an opened side of the cap-shaped yoke 11 of the aforementioned first embodiment. Each of the extending parts 31a and 31b has a facing curved surface 36 that faces each other, and is adjacent to an outer peripheral surface of the rotation axis body 7 at an even distance (gap).

These extending parts 31a and 31b are fixed on the space portion 32a so as to install the yoke 11 vertically. When doing so, the protrusion parts 32b are formed on the space portion 32a for positioning the yoke 11, and, on an installation surface (lower surface) of the extending parts 31a and 31b, concave parts 31c that are to be fitted to the protrusion parts 32b are formed, respectively.

In the light adjustment apparatus including a drive mechanism 30 that is configured in the above manner, an electromagnetic drive source similar to that of the aforementioned first embodiment is provided, which forms a magnetic circuit that generates a magnetic flux H passing through the rotation axis body 7. The magnetic force generated by this magnetic circuit causes the rotation arm part 8 to swing together with the rotation axis body 7, and stops the hole 8a on a predetermined light path (first light path, second light path).

Furthermore, although the outer peripheral surface of the shaft 33 shown in FIG. 7 is formed into a flat curved surface, the diameter may also be changed repeatedly into various sizes, and, by providing at least one annular waveform concave and convex on the outer peripheral surface, a surface that comes in contact with the inner surface of the hole 35c of the magnet 35 may be reduced to further reduce the frictional resistance.

In a normally used state, the light adjustment apparatus of the present embodiment configured in this manner has the rotation axis body 7 of the drive mechanism 30 held rotatably on the shaft 33 in a floated state from the base surface 32d, which is caused by a magnetic force generated by the magnet 35 inside the shaft 33 acting on the extending parts 31a and 31b of the yoke 31 that is comprised of a conductive material or a magnetically permeable material. The magnet 35 installed inside the rotation axis body 7 and the extending parts 31a and 31b of the yoke 31 configure a float prevention part that prevents the rotation axis body 7 from floating in an axial direction of the shaft 33 (or an axial direction of a rotational axis of the rotation axis body 7). By this float prevention part, even if a force to float the rotation axis body 7 in the axial direction of the shaft 33 is acted thereon by swinging, etc., the magnetic force (restraining force) generated by the magnet 35 causes the rotation axis body 7 to return to its original position, and prevents it from floating. That is, the position of the rotation axis body 7 would be magnetically restrained. Furthermore, even in the case where a shock is applied externally by dropping, etc. the optical equipment on which the light adjustment apparatus is mounted, the extending parts 31a and 31b abut the rotation arm part 8 adjacent to the rotation axis body 7 in order to hold the rotation axis body 7 so as not to fall out from the shaft 33.

Since the rotation axis body 7 is held rotatably by being fitted into the shaft 33 in a floated state from the base surface 32d by the magnetic force of the magnet 35, there is less frictional resistance applied to the rotation operation. Therefore, as long as it is within a range that can maintain a state in which the rotation arm part 8 abuts the inner side corner part 32c, the rotation axis body 7 can be operated appropriately even by less magnetic force than in the first embodiment. Aside from this, a retaining cap may also be attached at the top of the shaft 33 onto which the rotation axis body 7 is fitted so as to mechanically prevent the rotation axis body 7 from falling out of the shaft 33, without the rotation arm part 8 and the extending parts 31a and 31b coming in contact. The present embodiment has a configuration in which the magnet 35 is fitted into the pipe-shaped rotation axis body 7. However, the embodiment is not limited thereto. Therefore, the rotation axis body itself may be configured by a single magnet.

The object of the present invention is to provide a light adjustment apparatus that, by a compact size and simple driving mechanism, would realize a stable swing operation in which the light adjustment element is free from floating or rattling, and optical equipment which has the light adjustment apparatus mounted thereon.

The present invention is not limited to the exact embodiments described above; therefore, the present invention can be embodied by modifying the structural elements without departing from the gist of the invention when being implemented. In addition, various inventions can be made by properly combining the structural elements disclosed in the above embodiments.

The invention claimed is:

1. A light adjustment apparatus that acts on a light flux passing through a light path on the light path, the light adjustment apparatus comprising:
    a blade member having a distal end and a proximal end, the blade member being placed into and removed from the light path by being rotated about the proximal end in a direction perpendicular to the light path;
    a light adjustment element provided on the blade member, the light adjustment element being configured to act on the light flux when it is positioned on the light path by rotating the blade member, the light adjustment element being one of a diaphragm, a shutter, a lens, a shielding plate, or a filter;
    a rotation axis body comprising a magnet, the rotation axis body having a first end and a second end, the first end being provided on the proximal end of the blade member, the rotation axis body being formed such that a hole is produced at a position of a central axis;
    a shaft inserted in the hole, the shaft rotatably holding the rotation axis body, the shaft having a lower end and an upper end, the rotation axis body being movable along the shaft into a space adjacent to the second end;
    a support substrate that supports the lower end of the shaft; and
    a yoke facing a side surface of the rotation axis body, the yoke being configured to receive a magnetic force of the magnet included in the rotation axis body and move the rotation axis body away from the support substrate and into the space to float the rotation axis body with respect to the support substrate.

2. Optical equipment on which the light adjustment apparatus according to claim 1 is mounted.

3. An endoscope on which the light adjustment apparatus according to claim 1 is mounted.

* * * * *